(12) United States Patent
Chen et al.

(10) Patent No.: US 11,131,667 B2
(45) Date of Patent: Sep. 28, 2021

(54) TEST PLATFORM SYSTEM AND DETECTION METHOD BY USING THE SAME

(71) Applicant: National Taiwan University, Taipei (TW)

(72) Inventors: Chien-Fu Chen, Taipei (TW); Wen-Shin Yeh, Taipei (TW)

(73) Assignee: National Taiwan University, Taipei (TW)

(*) Notice: Subject to any disclaimer, the term of this patent is extended or adjusted under 35 U.S.C. 154(b) by 69 days.

(21) Appl. No.: 16/395,333

(22) Filed: Apr. 26, 2019

(65) Prior Publication Data

US 2019/0329241 A1    Oct. 31, 2019

(30) Foreign Application Priority Data

Apr. 27, 2018   (TW) .................. 107114505

(51) Int. Cl.
| | |
|---|---|
| *G01N 33/558* | (2006.01) |
| *G01N 33/543* | (2006.01) |
| *B01L 3/00* | (2006.01) |
| *G01N 21/78* | (2006.01) |

(52) U.S. Cl.
CPC ...... *G01N 33/54386* (2013.01); *B01L 3/5023* (2013.01); *B01L 3/502707* (2013.01); *G01N 21/78* (2013.01); *G01N 33/558* (2013.01); *B01L 2200/10* (2013.01); *B01L 2300/0825* (2013.01); *B01L 2300/126* (2013.01); *B01L 2300/168* (2013.01)

(58) Field of Classification Search
CPC ............ B01L 3/5023; B01L 3/502707; B01L 2300/168; B01L 2300/126; B01L 2200/10; B01L 2300/0825; G01N 33/558; G01N 33/54386; G01N 21/78
USPC ..... 422/400, 401, 420, 425, 430; 435/287.7, 435/287.9, 970, 805, 810; 436/169, 170, 436/514, 518, 530, 810
See application file for complete search history.

(56) References Cited

U.S. PATENT DOCUMENTS

| | | | |
|---|---|---|---|
| 4,717,656 A * | 1/1988 | Swanljung | ........... G01N 33/528 435/7.92 |
| 8,012,770 B2 * | 9/2011 | Siciliano | .......... G01N 33/56922 436/518 |

OTHER PUBLICATIONS

Schonhorn et al, "A device architecture for three-dimensional, patterned paper immunoassay", Lab Chip, 2014, 14, 4653-4658.*

* cited by examiner

*Primary Examiner* — Christopher L Chin
(74) *Attorney, Agent, or Firm* — Amin, Turocy & Watson, LLP

(57) ABSTRACT

The present disclosure provides a paper-based vertical flow test platform including: a detection portion; a movable conjugation portion having an enzyme-labelled protein; and an absorbent portion. The present disclosure further provides a detection method by using the same. With the folding and sliding design, the present disclosure can reduce the volume of specimen fluids used, and prevent the interference problem. Also, a portable diagnostic test platform is provided with ease of use, lower cost, higher sensitivity and longer storage period to meet requirements of point-of-care for the fast, simple and stable detection.

20 Claims, 14 Drawing Sheets

TEST PLATFORM SYSTEM AND DETECTION METHOD BY USING THE SAME

BACKGROUND

1. Technical Field

The present disclosure relates to a detecting system and a detection method by using the same, particularly to a vertical flow test device and a detection method by using the same.

In order to enable rapid control of the epidemic in developing countries where medical resources are scarce, the global medical community is actively investing in the development of "precise medical care." Among which includes the point-of-care (POC) system, which is used for testing and must meet the standard requirements of the World Health Organization (WHO) for parity, sensitivity, specificity, stability, ease of use, fast, no need for large equipment and ease to carry.

Microfluidic technology has been widely used in point-of-care systems in recent years through the miniaturization of components and combining of analysis systems, which require less specimens and reagents, and have the advantages of simplified operation and shortened analysis time. The paper-based microfluidic platform is combined with enzyme immunoassay to make the detection fluid flow to a specific zone by capillary action, so that the fluid part is immobilized to the surface of the platform by the specific binding of the antibody and the antigen, which is beneficial for qualitative or quantitative analysis and is economical as well.

The common paper-based test platform is mainly of a lateral-flow type, where the specimen flow path is long. Since the path flowing through the control group and the test group is the same, it is easy to cause the problem of large dead specimen volume and the interference of signals between the control group and the test group. In addition, since gold nanoparticles are mainly used as the color-coded markers, their weaker signals affect the identification result, and make quantitative detection impossible.

A few paper-based detecting platforms have vertical flow designs, and although they can partition the control zone and the test zone to solve the problem of fluid interference, the vertical flow test platform controls the fluid direction by a component membrane with different aperture sizes. Accordingly, they do not meet the needs for rapid detection and reduced specimen fluid volume.

Therefore, it is necessary to propose a test platform for quick detection, reduced requirement for specimen fluid volume, simple operation, and with high stability to solve the problems of the prior art.

SUMMARY

In order to solve the above-mentioned problems, the present disclosure provides a test platform system comprising a paper-based vertical flow test device, wherein the paper-based vertical flow test device comprises: a detection portion having a test zone and a control zone for receiving a specimen fluid containing a target protein; a conjugation portion having an enzyme-labelled protein, the conjugation portion being movably disposed above the detection portion to allow the conjugation portion to be pulled away from the detection portion or to cover the detection portion; and an absorbent portion having a multi-layer structure and being disposed below the detection portion, wherein the absorbent portion has a first absorbing zone and a second absorbing zone corresponding to the test zone and the control zone, respectively.

The present disclosure further provides a detection method by using the test platform system, comprising: contacting a specimen fluid containing the target protein with the test zone and the control zone of the detection portion of the paper-based vertical flow test device; covering a conjugation portion over the detection portion, and washing the conjugation portion with a washing buffer solution to specifically bind an enzyme-labelled protein to the target protein of the detection portion to form a conjugate; adding a substrate to color the conjugate; and obtaining a detection result from a change in the presented color.

By combining the folding and sliding design, the paper-based vertical test device of the present disclosure can reduce the volume of the specimen fluids used and avoid the problem of fluid interference in the control zone and the test zone, and improve the measurement accuracy. Furthermore, with the addition of the stabilizer, the prolonged storage period is sufficient to meet the World Health Organization's (WHO) standards for point-of-care.

BRIEF DESCRIPTION OF THE DRAWINGS

The disclosure can be more fully understood by reading the following detailed description of the embodiments, with reference made to the accompanying drawings, wherein.

DETAILED DESCRIPTION

Figure 1:
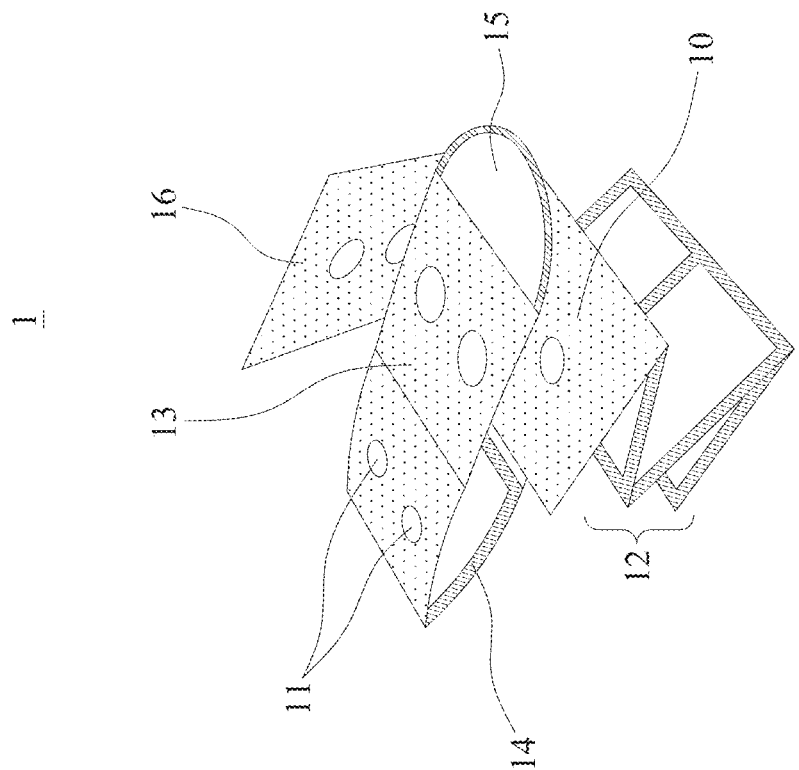
FIG. 1 is a schematic view showing a folded structure of a paper-based vertical test platform according to an embodiment of the present disclosure.

The following illustrative embodiments are provided to illustrate the present disclosure; these and other advantages and effects can be readily comprehended by those skilled in the art after reading the disclosure of this specification. The present disclosure can also be performed or applied by other different embodiments. The details of the specification may be based on different points and applications, and different modifications and variations can be devised without departing from the spirit of the present disclosure. In addition, all ranges and values herein are inclusive and combinable. Any value or point falling within the ranges recited herein, such as any integer, may be the minimum or maximum value to derive the subordinate range and the like.

In the present disclosure, a "target protein" means a protein detectable by a test platform.

In the present disclosure, an "adsorbing protein" means a protein which specifically binds to a conjugate of a target protein.

In the present disclosure, an "active agent" means a reaction reagent having a functional group reactive to the target protein.

In the present disclosure, a "coupling reaction" refers to a reaction process in which two independent chemical entities (for example, carboxymethylcellulose and the active agent) are combined into one compound.

In the present disclosure, a "coupling agent" means a catalyst for the coupling reaction; for example, carboxymethyl cellulose reacts with the coupling agent to form an unstable intermediate. At the beginning and end of the coupling reaction, the concentration of the coupling agent is unchanged.

According to the present disclosure, there is provided a paper-based vertical flow test platform comprising: a detection portion having a test zone and a control zone for receiving a specimen fluid having a target protein; and a conjugation portion comprising an enzyme-labelled protein, the conjugation portion being movably disposed above the detection portion to allow the conjugation portion to be pulled away from the detection portion or to cover the detection portion; and an absorbent portion having a multilayer structure and being disposed below the detection portion, wherein the absorbent portion has a first absorbing zone and a second absorbing zone corresponding to the test zone and the control zone, respectively.

In an embodiment, the absorbent portion forms a hydrophobic barrier to partition the fluids in the first absorbing zone and the second absorbing zone corresponding to the test zone and the control zone, respectively, to avoid the problem of fluid interference in the control zone and the test zone. The hydrophobic barrier can be made by any means that can achieve the purpose of partitioning the fluids in the first absorbing zone and the second absorbing zone, including but not limited to wax; hydrophobic plasma treatments with fluorine, fluorocarbon ($CF_x$), hydrocarbon ($CH_x$) chemistries, or the like; hydrophobic solvent coatings comprising polytetrafluoroethylene, manganese oxide polystyrene, or zinc oxide polystyrene; or other coatings, such as precipitated calcium carbonate, carbon nano-tube structures, silica nano-particles, tungstate, fluorinated silanes or fluoropolymer coatings.

The material of the paper-based vertical flow test platform can be made of cellulose fiber or nitrocellulose fiber; both of which are porous, so that the surface chemical, optical properties and porosity of the test platform are also crucial to the detection capability. The cellulose fiber has the advantages of low toxicity, hydrophilicity, low cost, good biodegradability, biocompatibility and porous structure, and is insoluble in water and most organic solvents; for example, the paper-based vertical flow test platform uses filter paper or chromatography paper as the main material. Moreover, the nitrocellulose is formed by nitration of parts of cellulose. The nitration reaction can strengthen the porosity of the cellulose, and with the surface being hydrolyzed by nitrification, the protein can directly form hydrogen bond with the nitro group of the nitrocellulose, so that the protein is immobilized on the surface of the nitrocellulose, and is not easily desorbed.

The enzyme-labelled protein refers to the protein being labelled with an enzyme and has the function to present a color, thereby facilitating interpretation of a detection result by the user. The enzyme of the enzyme-labelled protein may be selected from the group consisting of horseradish peroxidase (HRP), alkaline phosphatase (calf intestine alkaline phosphatase) and galactosidase (β-D-galactosidase). Further, the enzyme-labelled protein at the conjugation portion is temporarily adsorbed by electrostatic adhesion, so that it can be desorbed from the surface of the conjugation portion by other reagents and move.

In an embodiment, the enzyme-labelled protein is a human immunoglobulin G antibody with horseradish peroxidase (HRP).

In another embodiment, the human immunoglobulin G antibody having a horseradish peroxidase (HRP) is present in the conjugation portion in a range of from 0.01 to 0.3 μg.

In still another embodiment, the human immunoglobulin G antibody having a horseradish peroxidase (HRP) is present at 0.2 μg in the conjugation portion.

The detection portion further comprises a surfactant to adjust the hydrophilic and hydrophobic properties of the material of the paper-based vertical flow test platform to control the fluid flow rate.

In an embodiment, the paper-based vertical flow test platform includes: a connection portion connected to the conjugation portion and the detection portion; and a window portion connected to the conjugation portion and having two apertures corresponding to the test zone and the control zone, respectively, so as to cover the detection portion when the conjugation portion is pulled away from the detection portion.

Figure 2:
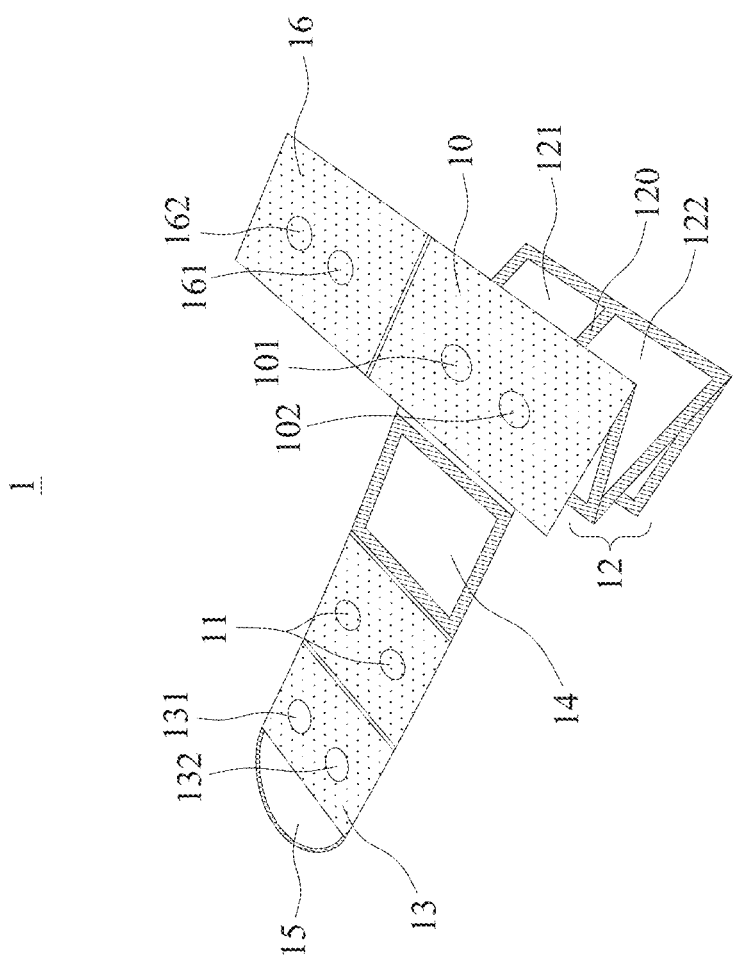
FIG. 2 is a schematic view showing an unfolded structure of a paper-based vertical test platform according to an embodiment of the present disclosure.

FIG. 1 and FIG. 2 show the folded structure and the unfolded structure of the paper-based vertical flow test platform of the present disclosure. The paper-based vertical flow test platform 1 includes: a detection portion 10 having a test zone 101 and a control zone 102 disposed at intervals on the same surface; a conjugation portion 11 comprising the enzyme-labelled protein being movably disposed over the detection portion 10 to allow the conjugation portion 11 to be pulled away from the detection portion 10 or to cover the detection portion 10; an absorbent portion 12 having a multi-layer structure and being disposed below the detection portion 10, wherein the absorbent portion 12 has a first absorbing zone 121 and a second absorbing zone 122 corresponding to the test zone 101 and the control zone 102, respectively; a window portion 13 connected to the conjugation portion 11 and having two apertures 131 and 132 corresponding to the test zone 101 and the control zone 102, wherein when the conjugation portion 11 is pulled away from the detection portion 10, the window portion 13 covers the detection portion 10; a connection portion 14 connected to the conjugation portion 11 and the detection portion 10; a pulling portion 15 optionally formed on one side of the window portion 13 for holding when pulling the conjugation portion 11 and the window portion 13 over the detection portion 10; and a top portion 16 connected to the detection portion 10 and having two apertures 161 and 162 corresponding to the test zone 101 and the control zone 102, thereby facilitating the user to drop the specimen fluid and the reagent, and directly observing the detection result through the aperture. In an embodiment of manufacturing the aforementioned absorbent portion 12, the paper is folded to form a continuous multi-folded multilayer structure. In addition, the hydrophobic barrier 120 is formed by wax to partition the first absorption zone 121 and the second absorption zone 122 corresponding to the test zone 101 and the control zone 102 respectively to absorb the fluid flowing down from the test zone 101 and the control zone 102. The detection portion 10, the conjugation portion 11, the absorbent portion 12, the window portion 13, the connection portion 14, and the top portion 16 are all made of paper; and also in this embodiment, each has a rectangular shape with four sides to facilitate the formation of the absorbent portion 12, the connection portion 14, and the top portion 16 on different sides of the detection portion 10, respectively. However, in various embodiments, the shape and location of the various portions are not limited.

Figure 3B:
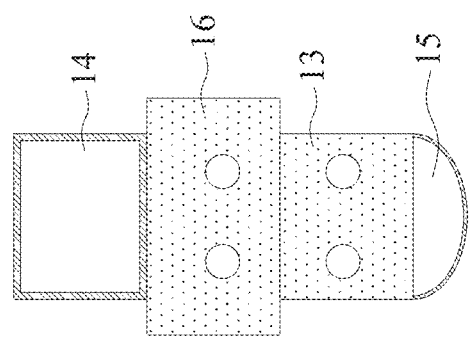
FIGS. 3A and 3B are top views of an embodiment of the paper-based vertical test platform according to embodiments of the present disclosure.
Figure 3A:
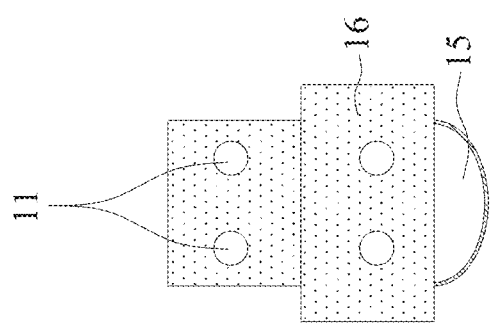

FIGS. 3A and 3B show embodiments of the paper-based vertical flow test platform of the present disclosure. FIG. 3A is a view showing an embodiment of the window portion 13 covering the detection portion 10. As shown in FIG. 3A, the top portion 16 is above the window portion 13. Further, FIG. 3B is a view showing an embodiment in which the conjugation portion 11 covers the detection portion 10.

Since the surface protein of the paper-based vertical flow test platform of the present disclosure, after being exposed to moisture for a longer time, is easily oxidized, isomerized and hydrolyzed, the storage period of the test platform is an important issue in order to apply the test platform to the portable point-of-care. The paper-based vertical flow test platform of the present disclosure further includes a stabilizer, wherein the stabilizer may be selected from the group consisting of a saccharide, a polyol, an amino acid or a salt to slow down denaturation of the protein during storage period.

In an embodiment, the weight percentage of the stabilizer is in a range of greater than 0 to less than 30% of the total composition of the conjugation portion.

In another embodiment, the stabilizing agent is a saccharide, and the saccharide acts as an inert substrate to inhibit movement of all protein molecules in the conjugation portion and the detection portion, thereby slowing down degradation of the protein, and increasing the free energy of protein denaturation. However, the proportion of the added saccharide should not be too high to avoid the color reaction of the test platform.

In an embodiment, the saccharide comprises sucrose, fucose or chitosan.

In another embodiment, the stabilizer is sucrose and fucose, and the concentration of sucrose is in the range of greater than 0% to less than 15%.

In an embodiment, the stabilizer is sucrose and fucose, wherein the weight ratio of the sucrose to fucose is 1:1, and the concentration of the sucrose is about 10%.

By means of the addition of the stabilizer, the paper-based vertical flow test platform of the present disclosure can be stored for a long period of time without affecting the detection result. In an embodiment, the paper-based vertical flow test platform can be stored at room temperature up to 90 days.

In an embodiment, the paper-based vertical flow test platform can be stored for up to 30 days at room temperature, and the detection result is still not affected.

In another embodiment, the paper-based vertical flow test platform has a storage period of 75 days in a refrigerated environment (at the temperature of about 4° C.), and does not affect the detection result.

In another embodiment, the paper-based vertical flow test platform has a storage period of 2 days in a 40° C. environment, and the detection effect is still not affected.

The paper-based vertical flow test platform of the present disclosure further includes a surface modification layer in the testing zone of the detection portion.

In an embodiment, the surface modification layer has an active ester group of the formula (I):

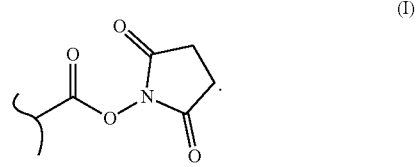

(I)

Figure 4:
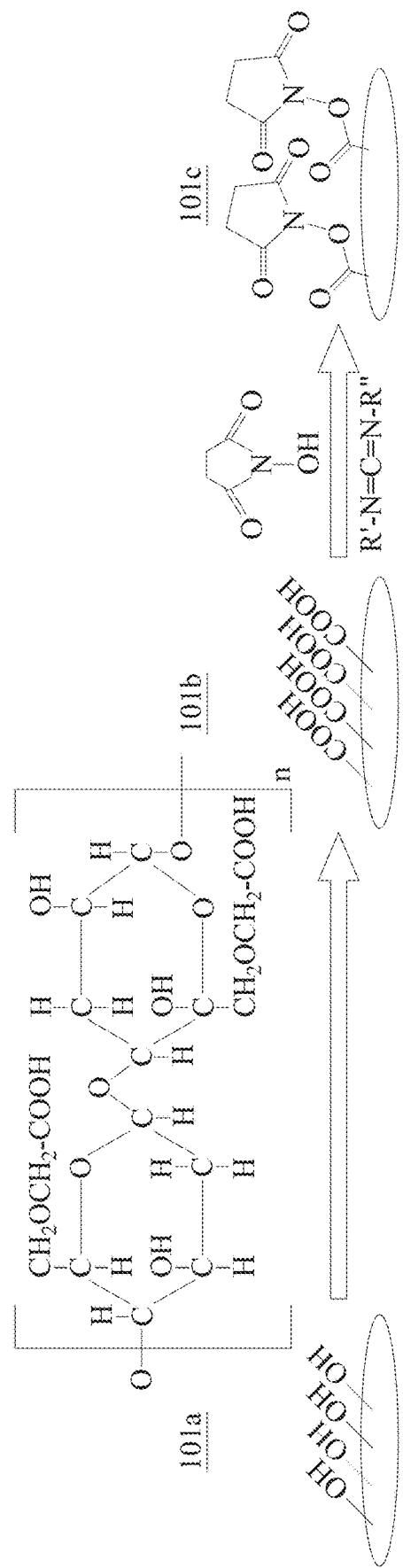
FIG. 4 is a flow chart showing a surface modification reaction of a first embodiment of the paper-based vertical test platform according to the present disclosure.

Please refer to FIG. 4, which is a flow chart showing the surface modification reaction of an embodiment of the paper-based vertical flow test platform of the present disclosure. The test zone of the detection portion is of a material of cellulose fibers. A test zone surface 101a having a plurality of hydroxyl groups is modified with carboxymethyl cellulose (CMC) to form a test zone surface 101b having a plurality of carboxyl groups. Then, a compound having a structure of (II) is used as a coupling agent:

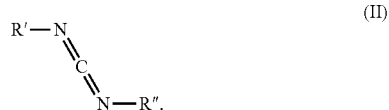

(II)

First, an unstable intermediate is formed with a carboxyl group, and the intermediate is further subjected to nucleophilic attack by a nitrogen atom of the active agent N-hydroxysuccinimide (NHS) to release the coupling agent, so as to form a test zone surface 101c having a structure of the formula (I) with an active ester group.

In another embodiment, the surface modification layer includes polyethylene glycol (PEG). By coating polyethylene glycol on the surface of the test zone of the detection portion, the anti-sticking effect can be achieved, thereby avoiding the non-specific adhesion; consequently, the background noise can be reduced, and the detection signal quality can be improved. Also, the sensitivity can also be increased.

In an embodiment of the paper-based vertical flow test platform of the present disclosure, the test zone of the detection portion further includes an amine-based adsorbing protein for specifically identifying the target protein, which is an application of the sandwich immunoassay method. The recommended concentration of the adsorbing protein is from 10 to 100 μg/ml, because the excessive adsorbing protein can easily cause a shadowing effect due to the spatial angle, where some of the binding sites are blocked by the adjacent adsorbing protein and fail to effectively bind to the target protein. However, if the content of the adsorbing protein is too low, the specificity of the test platform cannot be effectively improved, either.

Figure 5:
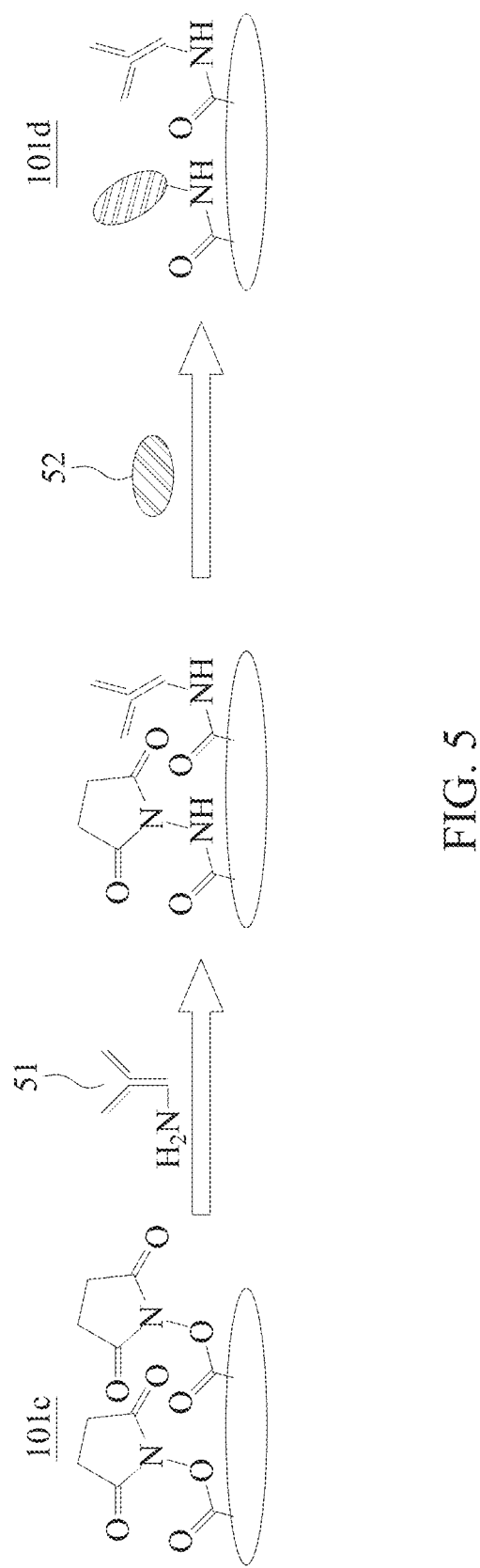
FIG. 5 is a flow chart showing a surface modification reaction of a second embodiment of the paper-based vertical test platform according to the present disclosure.

FIG. 5 shows the flowchart of the reaction of the paper-based vertical flow test platform. The amine group of the adsorbing protein 51 forms a chemical bond with the active ester group of the surface 101c of the test zone having an active ester group; then, the bovine serum albumin 52 is used to cover parts of the unbound active sites, which forms the surface of the test zone 101d having the amine-based adsorbing protein to avoid affecting the detection result by the direct binding reaction between the active site of the platform surface and the target protein. The bovine serum concentration is recommended to be 1 to 5%.

In an embodiment, the adsorbing protein is a human immunoglobulin G antibody, wherein the human immunoglobulin G antibody is recommended to be in an amount ranging from 5 to 200 ng. In another embodiment, the human immunoglobulin G antibody is 66 ng.

The present disclosure provides a method for using the above-mentioned paper-based vertical flow test platform, which comprises steps of contacting a specimen fluid containing a target protein with a test zone and a control zone of a detection portion of the paper-based vertical flow test platform; covering a conjugation portion over the detection portion, and washing the conjugation portion with a washing buffer solution to specifically bind an enzyme-labelled protein to the target protein of the detection portion to form a conjugate; adding a substrate to color the conjugate; and obtaining a detection result from a change in the presented color.

The target protein includes an antibody or an antigen. In an embodiment, the target protein having an amine group reacts with a surface of a paper-based vertical flow test platform having an active ester group to form an irreversible chemical bond in a short time. Consequently, it is difficult for the target protein to desorb.

The washing buffer solution includes bovine serum albumin and a phosphate buffer solution containing polyoxyethylene sorbitan monolaurate (Tween 20). Rinsing the conjugation portion and the detection portion with the washing buffer solution desorbs the enzyme-labelled protein of the conjugation portion, and removes the non-specific bond remaining in the detection portion as well, thereby reducing the interference of the background noise on the detection result. The recommended amount of the washing buffer solution is 10 to 500 μl, and the use of the washing buffer solution should not be in excess to avoid affecting the detection results and reducing the signal identification. In an embodiment, the recommended amount of the washing buffer solution is 100 μl.

In an embodiment, the enzyme-labelled protein may be an antibody with horseradish peroxidase (HRP), and the substrate capable of undergoing an enzyme reaction with the horseradish peroxidase can be one selected from the group consisting of potassium iodide (KI), 3,3',5,5'-tetramethylbenzidine (TMB), 3,3'-diaminobenzidine (DAB), 2,2-diazepine-bis(3-ethyl-benzothiazoline-6-sulfonate acid) diammonium salt (ABTS) and phosphorus phenylenediamine dihydrochloride (OPD), wherein 3,3',5,5'-tetramethylbenzidine is less toxic and can be used for coloring the substrate, which is blue. If the target protein is contained in the specimen fluid, the blue color can be observed by the naked eye. When the target protein concentration is extremely high, the blue color represented by the 3,3',5,5'-tetramethylbenzidine is dark blue, and the image analysis software can further analyze the color intensity; and after standardization, the blue intensity exhibited by the substrate can correspond to the actual concentration of the target protein for a further quantitative effect.

Based on the reaction of the enzyme-labelled protein and the substrate being a dynamic process, and that the color reaction generally needs a reaction termination reagent to end the reaction, the present disclosure determines the detection result by time control to reduce the reagent dosage. In an embodiment, the paper-based vertical flow test platform of the present disclosure presents the color on the conjugate 5 minutes after adding the substrate.

In order to make the target protein in the specimen fluid diffuse rapidly to the effective binding site to form a chemical bond, the temperature control is also a major factor. Appropriately increasing the temperature can accelerate the movement of the target protein and increase the probability of collision to accelerate the specific binding reaction. In an embodiment, the temperature of the specimen fluid is 25 to 40° C. However, the temperature of the specimen fluid should not be too high to avoid denaturation of the target protein and affect the specific binding ability.

Figure 6:
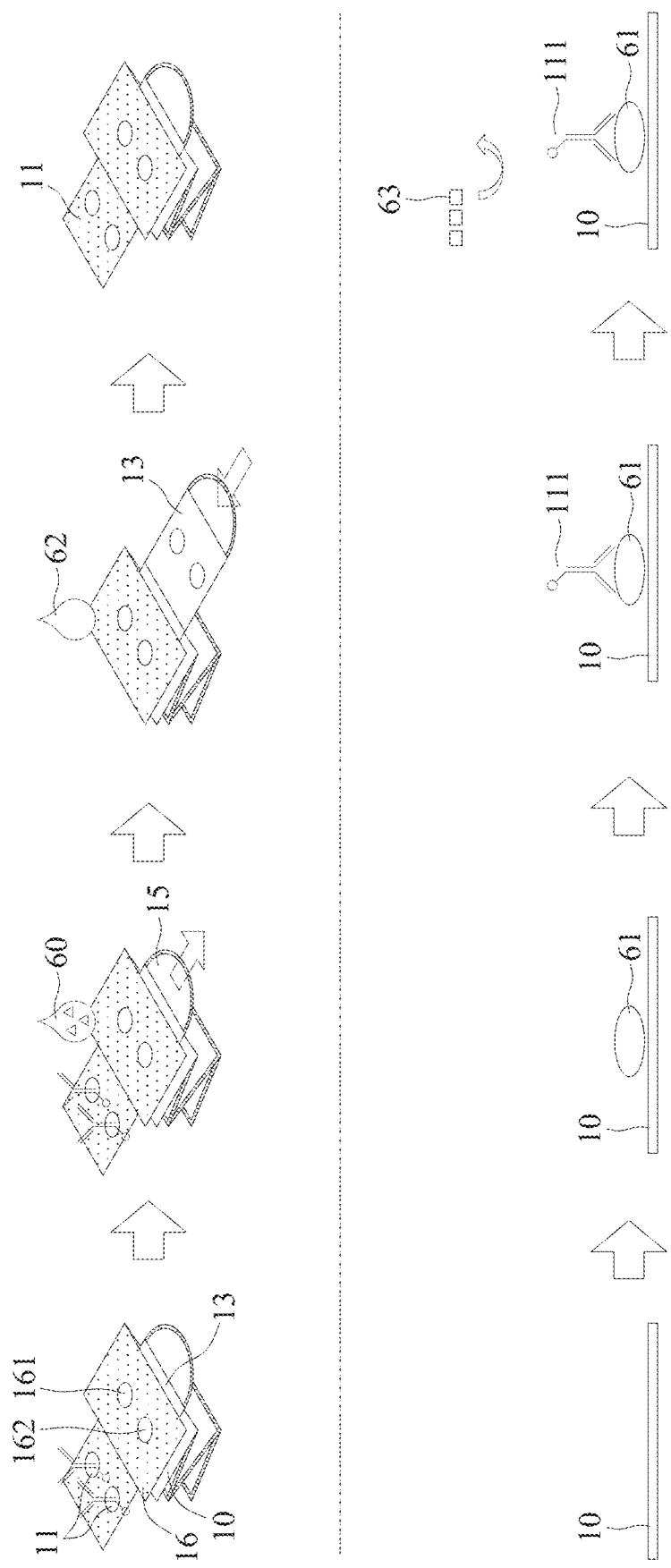
FIG. 6 is a flow chart showing a method for detecting a target protein according to a first embodiment of the paper-based vertical test platform of the present disclosure.

FIG. 6 shows a flow chart of a method for detecting a target protein by the first embodiment of the paper-based vertical flow test platform of the present disclosure, which includes steps of: adjusting a paper-based vertical flow test platform 1 to cover the detection portion 10 with the window portion 13; introducing the specimen liquid 60 containing the target protein 61 into the test zone 101 and the control zone 102 of the detection portion 10 below through the apertures 161 and 162 of the top portion 16 and the apertures 131 and 132 of the window portion 13, in which the binding of the target protein 61 with the surface of the test platform occurs; after switching the conjugation portion 11 to cover on the detection portion 10 by the pulling portion 15, washing the conjugation portion 11 with the washing buffer solution 62 to specifically bind the enzyme-labelled protein 111 to the target protein 61 of the detection portion 10, so as to form a conjugate; after returning the window portion 13 to cover the detection portion 10 by the pulling portion 15, adding the substrate 63 to color the conjugate; and obtaining the detection result from the presented color change.

In an embodiment, the target protein is a human immunoglobulin G antigen, and the enzyme-labelled protein can be a human immunoglobulin G antibody having horseradish peroxidase (HRP), and the substrate is 3,3',5,5'-Tetramethylbenzidine (TMB).

The detection of the human immunoglobulin G antigen by using the paper-based vertical flow test platform of the present disclosure not only has little detection error and improves the stability of detection, but also can detect a lower human immunoglobulin G antigen concentration at 0.1 ng/ml, wherein the specimen volume required for the specimen is only 3 μl, and the operation time of the whole detection is shorten to 7.1 minutes, and therefore has the advantages of rapid detection, reduced specimen volume and low cost.

Figure 7:
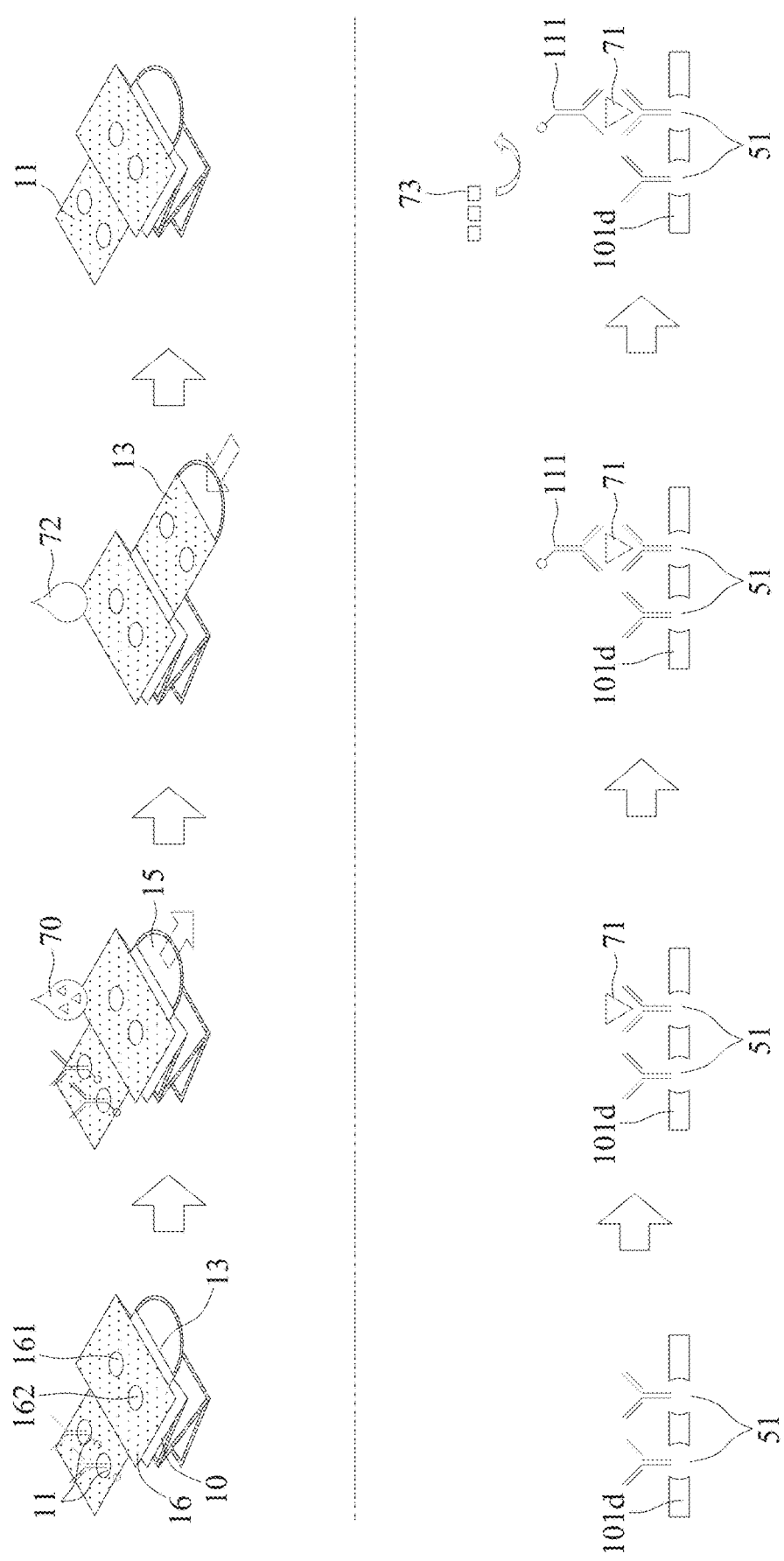
FIG. 7 is a flow chart showing a method for detecting a target protein of a second embodiment according to the paper-based vertical test platform of the present disclosure.

In another embodiment, the test zone of the paper-based vertical flow test platform of the present disclosure includes an amine-based adsorbing protein. FIG. 7 shows a flow chart of a method for detecting the target protein by the second embodiment of the paper-based vertical flow test platform of the present disclosure, which comprises steps of adjusting the paper-based vertical flow test platform 1 to cover the detection portion 10 with the window portion 13, wherein the surface of the test zone of the detecting platform is a test zone surface 101*d* comprising an amine-based adsorbing protein; introducing the specimen liquid 70 having the target protein 71 into the test zone 101 and the control zone 102 of the detection portion 10 below through the apertures 161 and 162 of the top portion 16 and the apertures 131 and 132 of the window portion 13, in which the binding of the target protein 71 with the adsorbing protein 51 on the surface 101*d* of the test zone with the amine-based adsorbing protein occurs; after switching the conjugation portion 11 to cover the detection portion 10 by the pulling portion 15, washing the conjugation portion 11 with the washing buffer solution 72 to specifically bind the enzyme-labelled protein 111 to the target protein 71 of the detection portion, so as to form a conjugate; after returning the window portion 13 to cover the detection portion 10 by the pulling portion 15, adding the substrate 73 to color the conjugate; and obtaining the detection result from the presented color change.

Figure 14:
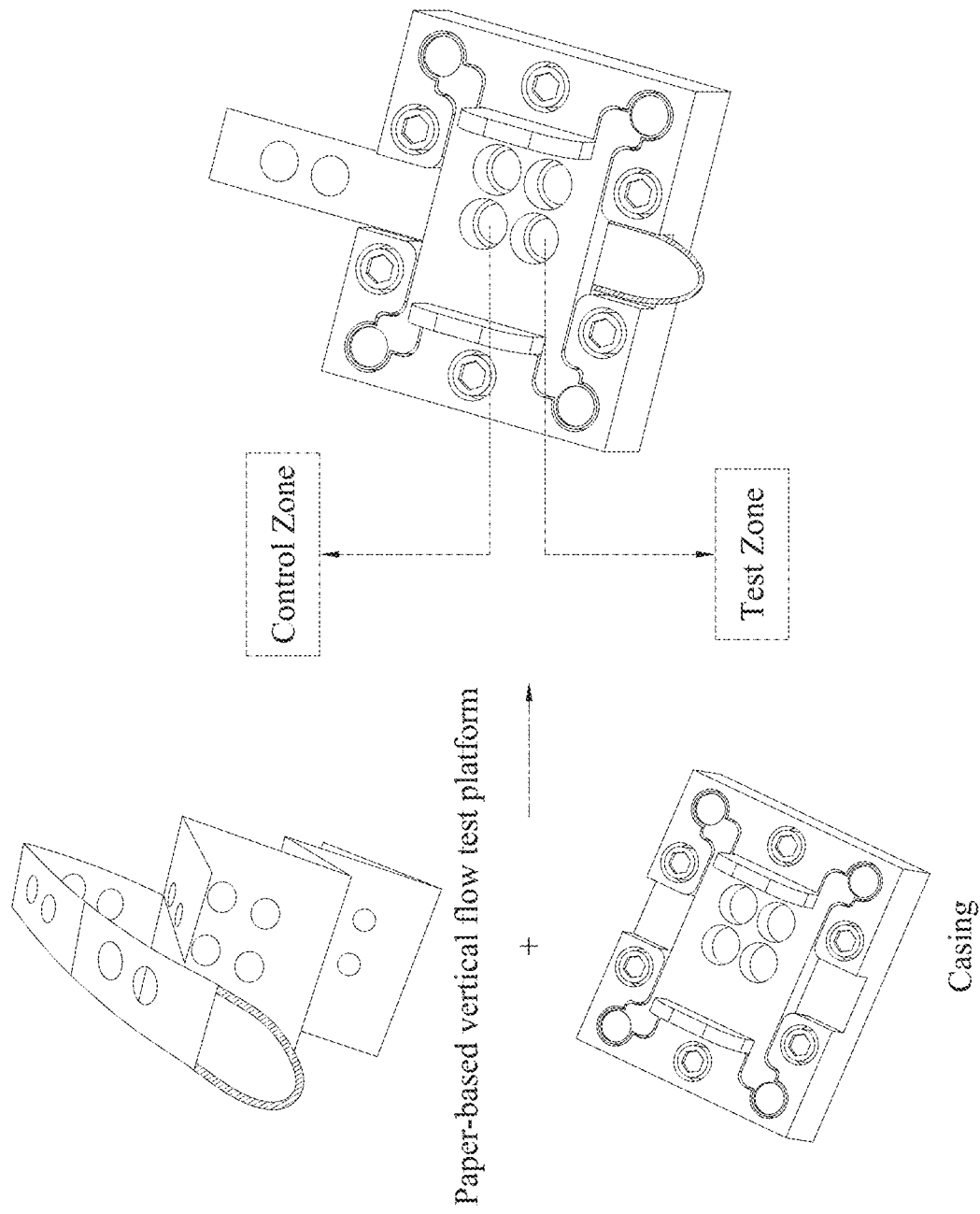
FIG. 14 is a diagram showing a casing used to house the paper-based vertical test platform according to an embodiment of the present disclosure.

In another embodiment, the paper-based vertical flow test platform further includes a casing to house the paper-based vertical flow test platform, as shown in FIG. 14. The casing provides support and protection to the paper-based vertical flow test platform and improves stability and reproducibility of the test results. The casing can be made of any material or in any shape as long as it does not hamper the function or interfere with the use of the paper-based vertical flow test platform. For example, a casing will have apertures corresponding to the test zone and the control zone of the detection portion of the paper-based vertical flow test platform to allow the receiving of specimen fluid.

In one embodiment, the paper-based vertical flow test platform is enclosed in a casing made of plastic. In other embodiments, material of the casings includes metal, carbon fiber or glass. In one embodiment, the casing is made by 3D printing.

By combining the folding and sliding design, the paper-based vertical test platform of the present disclosure can reduce the volume of the specimen fluids used and avoid the problem of fluid interference in the control zone and the test zone, and improve the measurement accuracy; through the addition of the stabilizer, the prolonged storage period is sufficient to meet the World Health Organization's (WHO) standards for point-of-care.

The present disclosure is further described in detail by way of examples as follows.

Preparation Example 1 of Paper-Based Vertical Flow Test Platform

Figure 8:
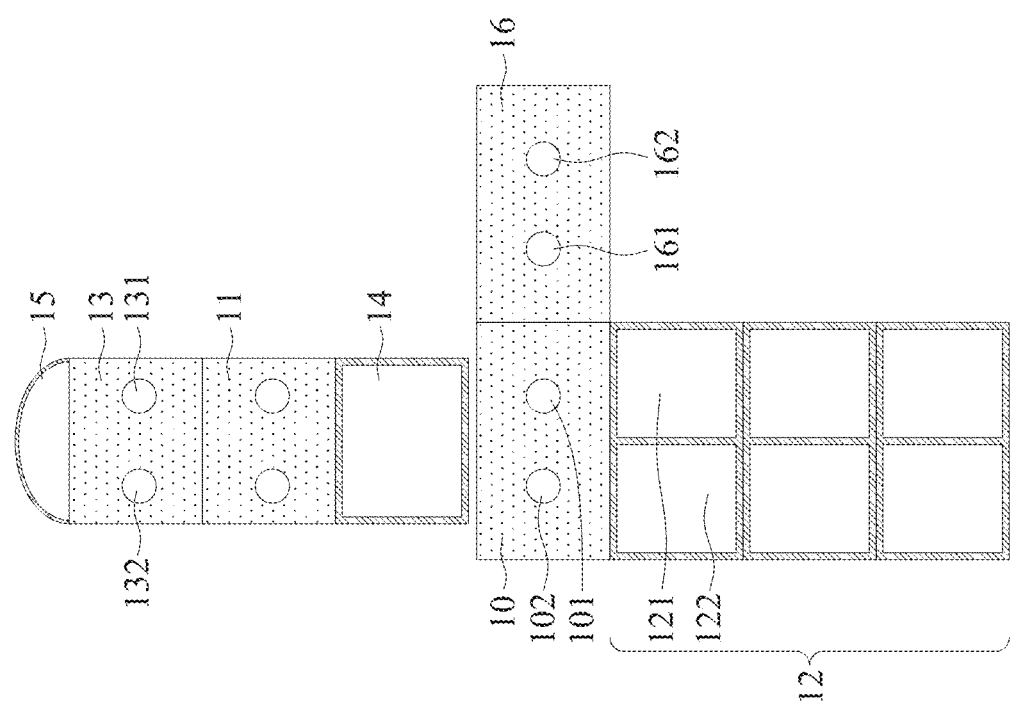
FIG. 8 is a diagram showing a hard wax print of the paper-based vertical test platform according to an embodiment of the present disclosure.

The cellulose test paper was used as the basic material. The designed pattern (as shown in FIG. 8) was printed on the test paper having solid wax with a wax printer, and then heated at 120° C. for 1 minute to melt the wax block and infiltrate into the fiber to form a hydrophobic barrier. After re-solidification, an absorbent portion 12 having a rectangular hydrophilic zone, a detection portion 10 having two circular hydrophilic zones, a conjugation portion 11, a window portion 13, and a top portion 16 were formed on the surface of the test paper. The two circular hydrophilic zones on the surface of the detection portion 10 have a diameter of about 5 mm, designated as the test zone 101 and the control zone 102. Apertures 131, 132, 161, and 162 were formed by the hole puncher in the circular hydrophilic zones of the window portion 13 and the top portion 16 of the test paper. Also, the apertures 131, 132, 161, and 162 correspond to the test zone 101 and the control zone 102 of the detection portion 10.

First, a calcium chloride solution having a concentration of 25 mmol was prepared in double distilled water and heated, and then 0.005 g of carboxymethylcellulose was placed in 10 ml of the above calcium chloride solution. The anhydroglucose unit of the carboxymethyl cellulose has 0.7 carboxymethyl group and a weight average molecular weight of 250,000; the temperature was raised to 40° C. on a hot plate and stirred for 15 minutes to completely dissolve the carboxymethyl cellulose to a concentration of 0.5% by weight. The solution of carboxymethylcellulose was then cooled at room temperature.

The prepared carboxymethylcellulose solution was applied to the test zone for surface modification reaction. After reacting for 20 minutes, it was dried by a hot plate, and the drying condition was 40° C. to form a surface modification layer.

Next, 1-ethyl-3-(3-dimethylaminopropyl)carbodiimide (EDC) at 0.1 M and N-hydroxysuccinimide (NHS) at 0.4 M were used to prepare sodium acetate and acetic acid buffer solution (pH 5.2±0.1 at a normal temperature of 25° C.) at a concentration of 10 mmol. After stirring for 10 minutes, it was coated onto the test zone above for reaction; after 30 minutes of reaction, the reaction was quenched with a 0.1 M of ethanolamine, and dried by a hot plate. The drying condition was 40° C. Then, a paper-based vertical flow test platform with an active ester group was completed.

Figure 9A:
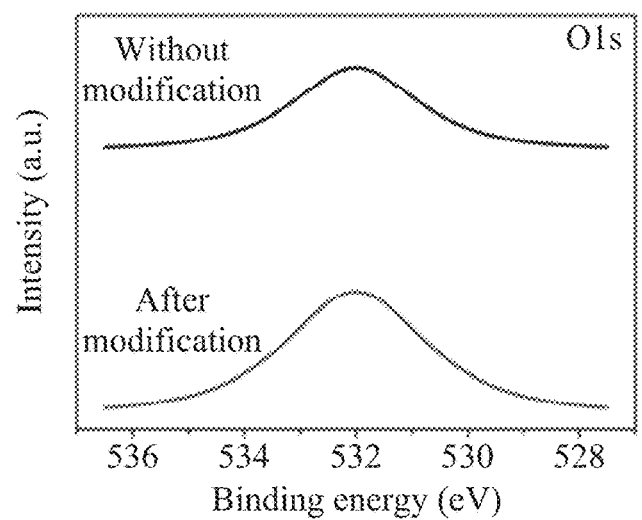
FIGS. 9A to 9C are energy spectrums of the surface structure of the paper-based vertical test platform according to an embodiment of the present disclosure analyzed by X-ray photoelectron spectroscopy (XPS)
Figure 9B:
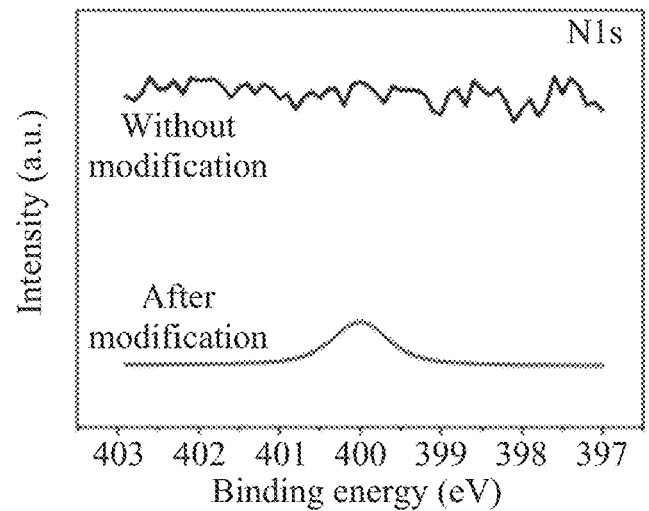
Figure 9C:
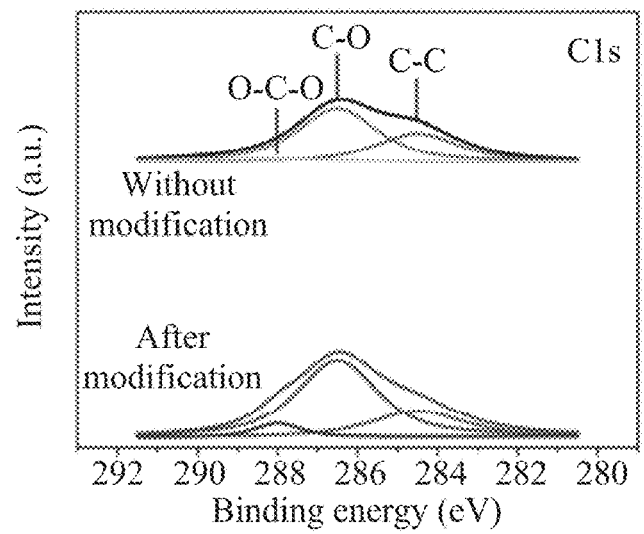

The surface of the test platform was analyzed by X-ray photoelectron spectroscopy (XPS). As shown in FIGS. 9A to 9C, the surface of the paper-based vertical flow test platform before and after surface modification was compared and analyzed. The signal intensity of the element carbon (C1s) and oxygen (O1s) were enhanced, and the signal peak of the nitrogen (N1s) element appears after the modification. As such, it was confirmed that the modification of the test platform has successfully produced the active ester group.

Next, the human immunoglobulin G antibody was chemically bonded to the active ester group on the surface of the test zone and immobilized on the surface of the test zone for the specific identification of the target protein, wherein the human immunoglobulin G antibody (Anti-HIgG Fab specific) solution was diluted to a concentration of 22 µg/ml in phosphate buffer solution before use, and the surface of the test zone was dried after adding 3 µl into the surface of the test zone. The drying temperature was 40° C., and the drying time was 4 minute. Further, after using a 1 to 5% bovine serum albumin (BSA) solution containing no polyoxyethylene sorbitan monolaurate phosphate buffer solution (Tween 20) to cover a portion of the unbound active site, a surface of the test zone immobilized with 66 ng human immunoglobulin G antibody was obtained.

On the other hand, a human immunoglobulin G antibody having a horseradish peroxidase (HRP) was retained on the surface of the above-mentioned conjugation portion, wherein the human immunoglobulin G antibody with horseradish peroxidase (HRP) (Anti-The HIgG-HRP) solution was diluted to a concentration of 66.5 µg/ml in phosphate buffer solution, and the surface of the test zone was dried after adding 3 µl into the surface of the test zone. The drying temperature was 40° C., and the drying time was 4 minutes. The content of the human immunoglobulin G antibody having the horseradish peroxidase (HRP) on the surface of the conjugation portion was 0.2 µg.

In addition, surface modification and antibody immobilization were not performed on the surface of the above control zone.

Experimental Example 1: Detection of Human Immunoglobulin G Antigen

First, one blank solution and 7 solutions of human immunoglobulin G (HIgG) antigen having a concentration of 0.01 to 10 ng/ml were prepared respectively as a detection standard solution, and were added one by one at a temperature of 25° C. to the paper-based vertical flow test platform prepared in the above Preparation Example 1.

Next, a phosphate buffer solution containing Tween 20 and 5% BSA was used as a washing buffer solution, and 100 µl of the washing buffer solution was pipetted into a control zone and a test zone; after drying, 3,3',5,5'-Tetramethylbenzidine (TMB) was introduced and subjected to an enzyme reaction for 5 minutes for color development, the image was taken with a microscope, and the color change was analyzed by an image analysis software.

Figure 10:
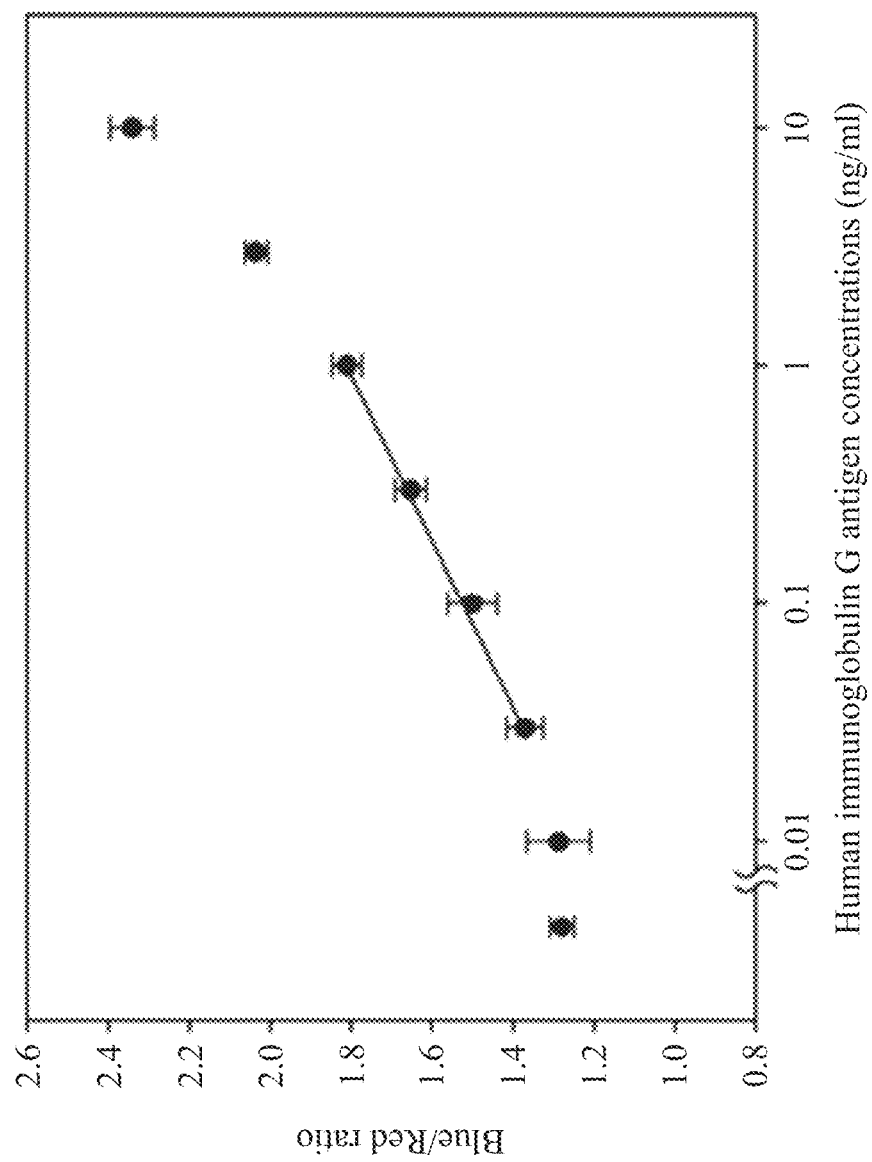
FIG. 10 is a scatter diagram of detecting human immunoglobulin G antigen concentrations and color changes by the paper-based vertical test platform according to an embodiment of the present disclosure.

FIG. 10 shows a scatter diagram of human immunoglobulin G antigen concentration and color change according to the experimental example. When the concentration of the G-type human immunoglobulin antigen was higher, the blue color becomes more and more obvious. From the experimental results, the dynamic linear range (optimal detection range) of the present embodiment was 0.03 to 1 ng/ml ($R^2=0.99$), and the detection error of each concentration was small, and the minimum detection limit (LOD) was obtained at 0.1 ng/ml.

Experimental Example 2: Storage Period Evaluation Test

Several paper-based vertical flow test platforms of Preparation Example 1 were prepared, and 3 µl of 10% fucose solution was added as a stabilizer to the conjugation portion, and then placed at −20° C. for 24 hours. After being placed in the freeze-dried bottle and moved to the freeze dryer, the droplets on the surface of the test platforms were sublimated into a gaseous state. After the vacuum was broken, the test platforms with the stabilizer were placed in the zipper bag and placed at room temperature (at about 25° C.). On Days 0, 1, 2, 5, 10, 15, 30, 45, 60, 75, 90, 105 and 120 after, the test platforms were taken out respectively, and 3 µl of TMB was added directly into the conjugation portion and subjected to an enzyme reaction for 5 minutes; the color development was observed, and the storage period of the test platform was evaluated.

The detection activity signal intensity of the paper-based vertical flow test platform was obtained by substituting a blue/red ratio (B/R value) of the color:

$$\text{Detection activity signal intensity}(\%) = \frac{(B/R \text{ ratio of Day } X) - 1.086}{(B/R \text{ ratio of Day } 0) - 1.086} \times 100$$

Figure 11:
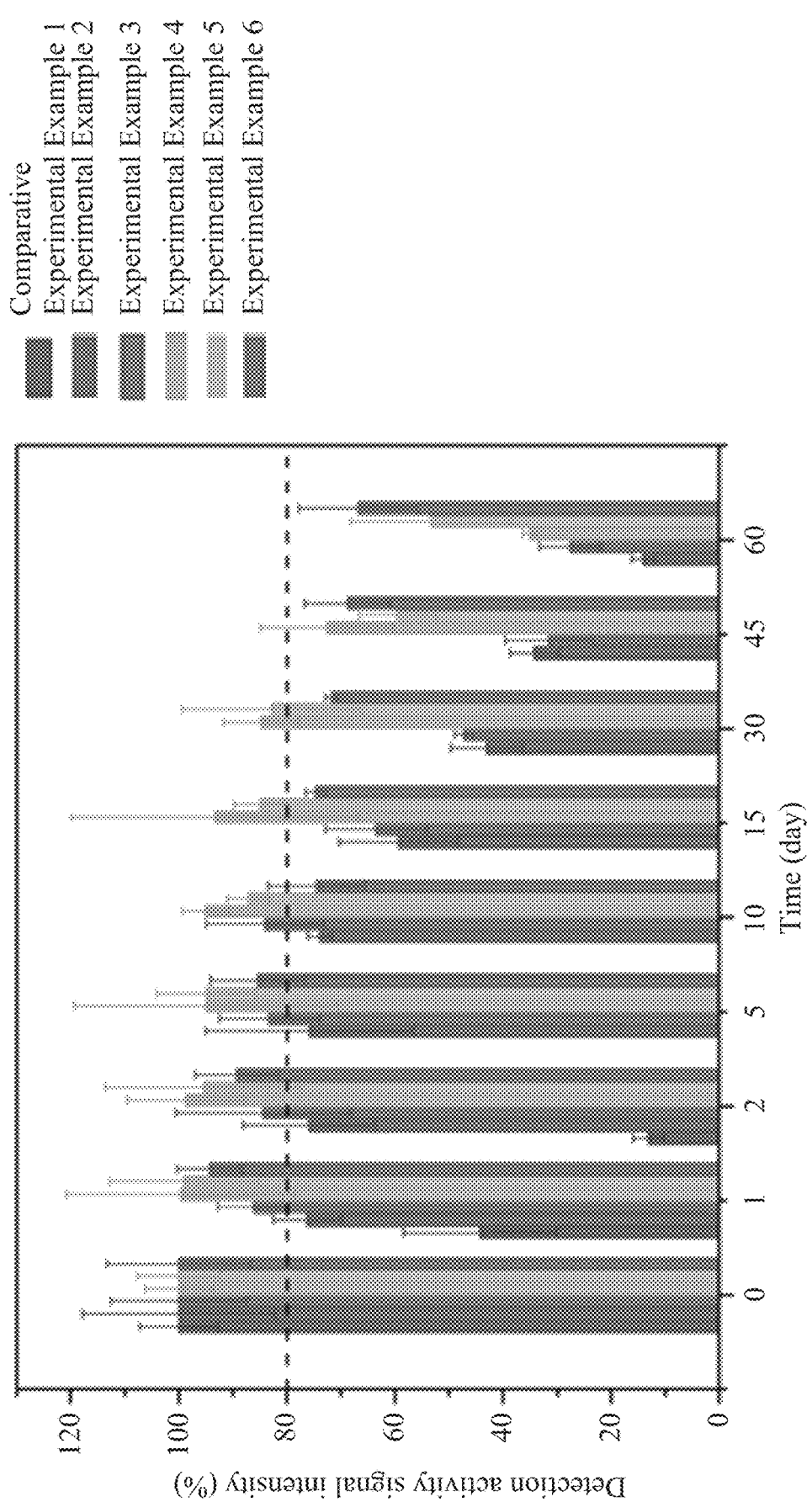
FIG. 11 is a diagram showing changes of detection activity signal intensities as a result of stabilizer concentrations in the paper-based vertical test platform at room temperature according to an embodiment of the present disclosure, wherein time points from left to right respectively represent Comparative Experimental Example 1, Experimental Example 2, Experimental Example 3, Experimental Example 4, Experimental Example 5, and Experimental Example 6; and Comparative Experimental Example 1 is almost completely degraded on Day 5, and no signal intensity is shown.

The change of the detection activity signal intensity of each test platform was shown in FIG. 11.

Experimental Examples 3 to 6: Storage Period Evaluation Test

The treatment methods of Experimental Examples 3 to 6 were the same as those of Experimental Example 2, except that the composition of the flow stabilizer was as shown in Table 1. The influence of the composition of the different stabilizers on the storage period of the test platform was evaluated as shown in FIG. 11.

Experimental Examples 7 to 11: Storage Period Evaluation Test

Figure 12:
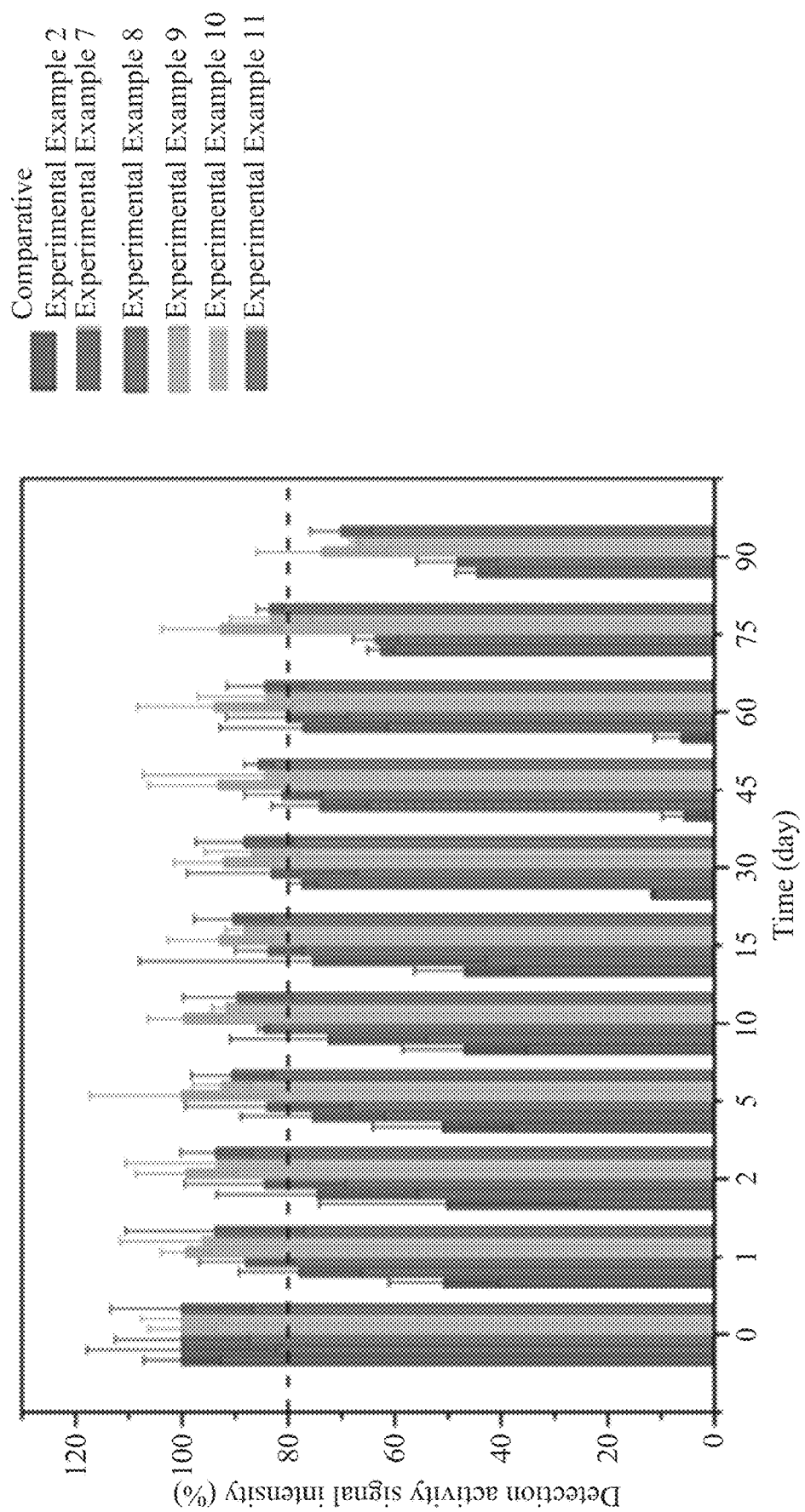
FIG. 12 is a diagram showing changes of detection activity signal intensities as a result of stabilizer concentrations in the paper-based vertical test platform at 4° C. according to an embodiment of the present disclosure, wherein time points from left to right respectively represent Comparative Experimental Example 2, Experimental Example 7, Experimental Example 8, Experimental Example 9, Experimental Example 10, and Experimental Example 11; and the signal intensity is too low on Day 75 and Day 90, and the signal intensity of Comparative Experimental Example 2 is not shown.

The treatment methods of Experimental Examples 7 to 11 were the same as those of Experimental Example 2, except that the ambient temperature was 4° C. and the composition of the stabilizer was as shown in Table 1. The influence of the composition of the different stabilizers on the storage period of the test platform was evaluated as shown in FIG. 12.

Experimental Examples 12 to 16: Storage Period Evaluation Test

Figure 13:
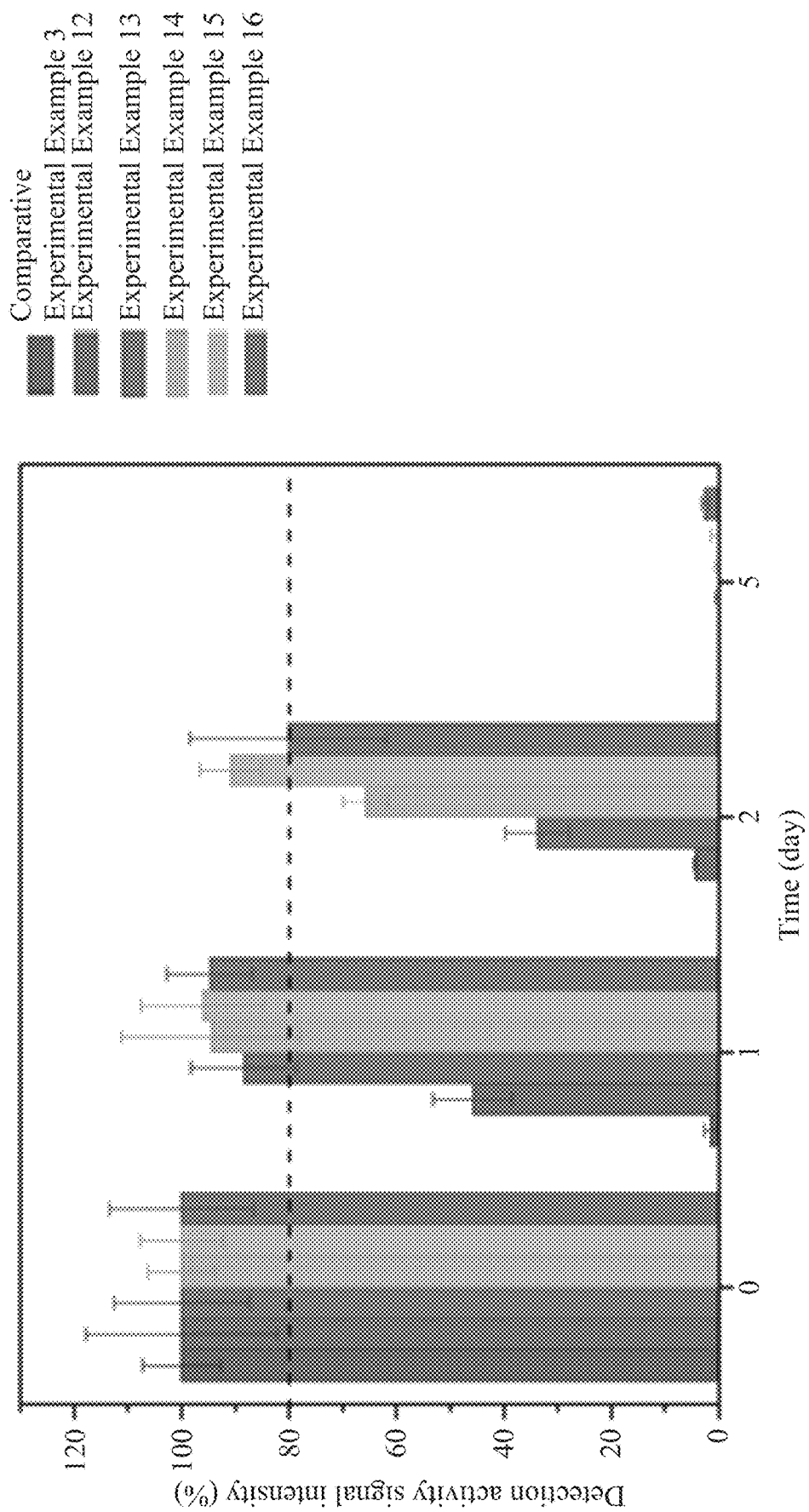
FIG. 13 is a diagram showing changes of detection activity signal intensities as a result of stabilizer concentrations in the paper-based vertical test platform at 40° C. according to an embodiment of the present disclosure, wherein time points from left to right respectively represent Comparative Experimental Example 3, Experimental Example 12, Experimental Example 13, Experimental Example 14, Experimental Example 15, and Experimental Example 16; the signal intensity of Comparative Experimental Example 3 is not shown on Day 2 because the signal intensity is too low; and due to the signal intensity on Day 5, only the signal intensity of Experimental Example 16 is shown.

The treatment methods of Experimental Examples 12 to 16 were the same as those of Experimental Example 2, except that the ambient temperature was 40° C. and the composition of the stabilizer was as shown in Table 1. The influence of the composition of the different stabilizers on the storage period of the test platform was evaluated as shown in FIG. 13.

Comparative Experimental Examples 1 to 3: Storage Period Evaluation Test

The treatment method of Comparative Experimental Example 1 was the same as those of Experimental Example 2, except that no stabilizer was added to the conjugation portion. The ambient temperature was as shown in Table 1, and the influence of the composition of the different stabilizers on the storage period of the test platform was evaluated.

TABLE 1

| | Ambient temperature | Composition of stabilizer | |
|---|---|---|---|
| | | Sucrose concentration (%) | Fucose concentration (%) |
| Experimental Example 2 | 25° C. | 0 | 10 |
| Experimental Example 3 | | 5 | 5 |
| Experimental Example 4 | | 10 | 0 |
| Experimental Example 5 | | 10 | 10 |
| Experimental Example 6 | | 15 | 15 |
| Comparative Experimental Example 1 | | 0 | 0 |
| Experimental Example 7 | 4° C. | 0 | 10 |
| Experimental Example 8 | | 5 | 5 |
| Experimental Example 9 | | 10 | 0 |
| Experimental Example 10 | | 10 | 10 |
| Experimental Example 11 | | 15 | 15 |
| Comparative Experimental Example 2 | | 0 | 0 |
| Experimental Example 12 | 40° C. | 0 | 10 |
| Experimental Example 13 | | 5 | 5 |
| Experimental Example 14 | | 10 | 0 |
| Experimental Example 15 | | 10 | 10 |
| Experimental Example 16 | | 15 | 15 |
| Comparative Experimental Example 3 | | 0 | 0 |

From FIG. 11, Comparative Experimental Example 1 without adding any stabilizer at room temperature has almost completely degraded on Day 5, while Experimental Examples 3 to 6 can still maintain the detection activity signal intensity of more than 80%. As the concentration of the added stabilizer increases, the degree of degradation of the enzyme-labelled protein in the conjugation portion also slows down. The storage period of Experimental Example 3 was about 10 days, and the storage period of Experimental Example 4 and Experimental Example 5 was about 30 days. The storage period of Example 6 was about 5 days.

From FIG. 12, at the ambient temperature of 4° C., Comparative Experimental Example 2 without adding any stabilizer was almost completely degraded on Day 75, while Experimental Examples 9 to 11 were able to maintain the detection activity signal intensity of more than 80%. As the concentration of the added stabilizer increased, the degree of degradation of the enzyme-labelled protein of the conjugation portion also slowed down, and the storage periods of Experimental Examples 9 to 11 were all 75 days.

From FIG. 13, at the ambient temperature of 40° C., Comparative Experimental Example 3 without adding any stabilizer was almost completely degraded on Day 2, and Experimental Example 15 was Able to Maintain the Detection Activity Signal Intensity of More than 80%

Therefore, when using sucrose and fucose with a weight ratio of 1:1 as a stabilizer, the paper-based vertical flow test platform has good detection stability and long storage period, and is one of the best mode embodiments.

In conclusion, the present disclosure combines folding and sliding design to enable a paper-based vertical flow test platform with reduced specimen fluid volume and avoid fluid interference in the control zone and the test zone, and improves measurement accuracy; and the addition of stabilizers extends storage period to meet World Health Organization (WHO) standards for point-of-care.

The above embodiments were merely illustrative and were not intended to limit the present disclosure. Modifications and variations of the above-described embodiments can be made by those skilled in the art without departing from the spirit and scope of the disclosure. Therefore, the scope of the present disclosure is defined by the scope of the appended claims. As long as the effects and implementation purposes of the present disclosure are not affected, they should be encompassed in this technical disclosure.

What is claimed is:

1. A test platform system, comprising:
   a paper-based vertical flow test device, comprising:
      a detection portion for receiving a specimen fluid containing a target protein, wherein the detection portion has a test zone and a control zone disposed at intervals on the same surface;
      a conjugation portion having an enzyme-labelled protein, the conjugation portion being movably disposed above the detection portion to allow the conjugation portion to be pulled away from the detection portion or to cover the detection portion; and
      an absorbent portion having a multi-layer structure and being disposed below the detection portion, wherein the absorbent portion has a first absorbing zone and a second absorbing zone corresponding to the test zone and the control zone, respectively.

2. The test platform system of claim 1, wherein the paper-based vertical flow test device is made of a material of cellulose fiber or nitrocellulose fiber, and further comprises a hydrophobic barrier in the absorbent portion for partitioning fluids of the first absorbing zone and the second absorbing zone.

3. The test platform system of claim 2, wherein the hydrophobic barrier comprises: wax; hydrophobic plasma treatment with fluorine, fluorocarbon ($CF_x$) or hydrocarbon ($CH_x$) chemistries; hydrophobic solvent coating including polytetrafluoroethylene, manganese oxide polystyrene, or zinc oxide polystyrene; or coatings with precipitated calcium carbonate, carbon nano-tube structures, silica nanoparticles, tungstate, fluorinated silanes or fluoropolymers.

4. The test platform system of claim 1, wherein the paper-based vertical flow test device further comprises:
   a connection portion connected to the conjugation portion and the detection portion; and
   a window portion connected to the conjugation portion and having two apertures corresponding to the test zone and the control zone, respectively,
   wherein when the conjugation portion is pulled away from the detection portion, the window portion covers the detection portion.

5. The test platform system of claim 1, wherein the enzyme-labelled protein is a human immunoglobulin G antibody having a horseradish peroxidase (HRP) contained in the conjugation portion in an amount of from 0.01 μg to 0.3 μg.

6. The test platform system of claim 1, wherein at least one of the conjugation portion and the detection portion further comprises a stabilizer.

7. The test platform system of claim 6, wherein the stabilizer is a saccharide, a polyol, an amino acid or a salt, and wherein the saccharide is selected from the group consisting of sucrose, fucose and chitosan.

8. The test platform system of claim 6, wherein the conjugation portion comprises the stabilizer, and the stabilizer has a weight percentage in a range of from greater than 0% to less than 30% of a total composition of the conjugation portion.

9. The test platform system of claim 8, wherein the stabilizer includes sucrose and fucose, and the sucrose has a concentration in a range of from greater than 0% to less than 15%.

10. The test platform system of claim 9, wherein the sucrose has a concentration of about 10% and a weight ratio of sucrose to fucose is 1:1.

11. The test platform system of claim 1, wherein the test zone further comprises a surface modification layer having an active ester group of formula (I):

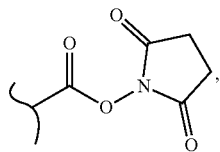

(I)

or
including polyethylene glycol (PEG).

12. The test platform system of claim 1, wherein the target protein comprises an antibody or an antigen, and wherein the target protein is formed of a human immunoglobulin G antigen.

13. The test platform system of claim 1, wherein the test zone comprises an amine-based adsorbing protein for specific identification of the target protein, and wherein the amine-based adsorbing protein is a human immunoglobulin G antibody.

14. The test platform system of claim 13, wherein the human immunoglobulin G antibody is present in the test zone in an amount of from 5 ng to 200 ng.

15. The test platform system of claim 1, further comprises a casing to house the paper-based vertical flow test device.

16. The test platform system of claim 1, wherein the paper-based vertical flow test device has a storage period of up to 90 days at room temperature.

17. A detection method by using the test platform system of claim 1, comprising:
contacting a specimen fluid containing the target protein with the test zone and the control zone of the detection portion of the paper-based vertical flow test device;
covering the conjugation portion over the detection portion, and washing the conjugation portion with a washing buffer solution to specifically bind the enzyme-labelled protein to the target protein of the detection portion to form a conjugate;
adding a substrate to color the conjugate; and
obtaining a detection result from a change in the presented color.

18. The detection method of claim 17, wherein the conjugate presents the color after 5 minutes of adding the substrate.

19. The detection method of claim 17, wherein the specimen fluid is present in a temperature of from 25° C. to 40° C.

20. The detection method of claim 17, wherein the target protein has a minimum detection limit of 0.1 ng/ml.

* * * * *